(12) United States Patent
Parker et al.

(10) Patent No.: US 11,484,350 B2
(45) Date of Patent: Nov. 1, 2022

(54) SPLIT TOWER FOR A BONE ANCHOR

(71) Applicant: Zimmer Biomet Spine, Inc., Westminster, CO (US)

(72) Inventors: Jared Parker, Denver, CO (US); Michael Funk, Broomfield, CO (US); Randall G. Mast, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 7 days.

(21) Appl. No.: 16/657,234

(22) Filed: Oct. 18, 2019

(65) Prior Publication Data
US 2020/0187987 A1     Jun. 18, 2020

Related U.S. Application Data

(60) Provisional application No. 62/779,255, filed on Dec. 13, 2018.

(51) Int. Cl.
*A61B 17/70*     (2006.01)

(52) U.S. Cl.
CPC .................................. *A61B 17/708* (2013.01)

(58) Field of Classification Search
CPC ............ A61B 17/7077; A61B 17/7079; A61B 17/7085; A61B 17/708
See application file for complete search history.

(56) References Cited

U.S. PATENT DOCUMENTS

| | | | |
|---|---|---|---|
| 8,211,110 B1 | 7/2012 | Corin et al. | |
| 8,439,922 B1 | 5/2013 | Arnold et al. | |
| 8,603,094 B2 | 12/2013 | Walker et al. | |
| 9,192,415 B1 | 11/2015 | Arnold et al. | |
| 9,211,149 B2 | 12/2015 | Hoefer et al. | |
| 9,220,543 B2 | 12/2015 | Walker et al. | |
| 9,333,012 B2 * | 5/2016 | Beale | A61B 17/7076 |
| 9,370,383 B2 | 6/2016 | Parker et al. | |
| 9,492,209 B2 | 11/2016 | Biedermann et al. | |
| 9,629,661 B2 | 4/2017 | Kraus | |
| 9,980,758 B2 | 5/2018 | Abidin | |
| 10,245,082 B2 | 4/2019 | Parker et al. | |
| 10,426,527 B2 | 10/2019 | Doose et al. | |
| 11,096,724 B2 | 8/2021 | Parker et al. | |
| 2002/0116006 A1 | 8/2002 | Cohen | |
| 2005/0131408 A1 | 6/2005 | Sicvol et al. | |
| 2006/0074418 A1 | 4/2006 | Jackson | |

(Continued)

FOREIGN PATENT DOCUMENTS

WO    WO-2014144274 A1    9/2014

OTHER PUBLICATIONS

U.S. Appl. No. 13/841,405 U.S. Pat. No. 9,370,383, filed Mar. 15, 2013, Minimally Invasive Splitable Pedicle Screw Extender.

(Continued)

*Primary Examiner* — Eduardo C Robert
*Assistant Examiner* — Holly Joanna Lane

(57) ABSTRACT

An anchor extender can be couplable to a bone anchor and can include an outer sleeve, an inner sleeve, and a lock. The lock can be operable to translate the inner sleeve relative to the outer sleeve between a locked position and an unlocked position to secure the inner sleeve and the outer sleeve to a head of the bone anchor in the locked position and to release the inner sleeve and the outer sleeve from the head of the bone anchor in the unlocked position.

18 Claims, 11 Drawing Sheets

(56) References Cited

U.S. PATENT DOCUMENTS

| | | | |
|---|---|---|---|
| 2006/0079894 A1 | 4/2006 | Colleran et al. | |
| 2006/0079909 A1 | 4/2006 | Runco et al. | |
| 2007/0233079 A1 | 10/2007 | Fallin et al. | |
| 2008/0077134 A1 | 3/2008 | Dziedzic et al. | |
| 2009/0143828 A1 | 6/2009 | Stad et al. | |
| 2009/0149892 A1 | 6/2009 | Stad et al. | |
| 2011/0034962 A1 | 2/2011 | Dunbar, Jr. et al. | |
| 2011/0313463 A1 | 12/2011 | Mclean | |
| 2012/0022594 A1 | 1/2012 | Walker et al. | |
| 2012/0035668 A1* | 2/2012 | Manninen | A61B 17/7086 606/305 |
| 2012/0116460 A1 | 5/2012 | Gorek | |
| 2013/0245702 A1* | 9/2013 | McBride | A61B 17/7076 606/305 |
| 2013/0245705 A1 | 9/2013 | Mcbride et al. | |
| 2013/0261679 A1 | 10/2013 | Mcbride et al. | |
| 2013/0336823 A1* | 12/2013 | Ophardt | F04B 7/00 417/447 |
| 2014/0039567 A1 | 2/2014 | Hoefer et al. | |
| 2014/0052187 A1 | 2/2014 | Mcbride et al. | |
| 2014/0148865 A1* | 5/2014 | Hennard | A61B 17/7086 606/86 A |
| 2014/0277200 A1* | 9/2014 | Parker | A61B 17/7037 606/86 A |
| 2014/0316475 A1* | 10/2014 | Parikh | A61B 17/7085 606/86 A |
| 2015/0039035 A1 | 2/2015 | Krüger | |
| 2015/0051648 A1 | 2/2015 | May et al. | |
| 2015/0066042 A1 | 3/2015 | Cummins et al. | |
| 2015/0073485 A1 | 3/2015 | Butler | |
| 2015/0359571 A1* | 12/2015 | Biedermann | A61B 17/7032 606/246 |
| 2016/0338744 A1* | 11/2016 | Parker | A61B 17/7037 |
| 2017/0079696 A1 | 3/2017 | Walker et al. | |
| 2017/0164985 A1 | 6/2017 | Reitblat et al. | |
| 2018/0000521 A1* | 1/2018 | Arnold | A61B 17/7083 |
| 2018/0008318 A1 | 1/2018 | Fiechter et al. | |
| 2019/0223924 A1 | 7/2019 | Parker et al. | |
| 2019/0343558 A1* | 11/2019 | Farmer | A61B 17/708 |
| 2020/0187988 A1* | 6/2020 | Farmer | A61B 17/862 |
| 2021/0085365 A1* | 3/2021 | Rosenthal | A61F 5/08 |

OTHER PUBLICATIONS

U.S. Appl. No. 15/160,373 U.S. Pat. No. 10,245,082, filed May 20, 2016, Minimally Invasive Splitable Pedicle Screw Extender.

U.S. Appl. No. 16/270,223, filed Feb. 7, 2019, Minimally Invasive Splitable Pedicle Screw Extender.

"U.S. Appl. No. 16/270,223, Non Final Office Action dated Dec. 31, 2020", 18 pgs.

"U.S. Appl. No. 16/270,223, Response filed Jan. 21, 2021 to Non Final Office Action dated Dec. 31, 2020", 11 pgs.

"European Application Serial No. 19215706.3, Response filed Dec. 17, 2020 to Extended European Search Report dated May 12, 2020", 3 pgs.

"European Application Serial No. 19215706.3, Extended European Search Report dated May 12, 2020", 9 pages.

"U.S. Appl. No. 13/841,405, Advisory Action dated Jan. 21, 2016", 5 pgs.

"U.S. Appl. No. 13/841,405, Final Office Action dated Oct. 1, 2015", 19 pgs.

"U.S. Appl. No. 13/841,405, Non Final Office Action dated Apr. 23, 2015", 15 pgs.

"U.S. Appl. No. 13/841,405, Notice of Allowance dated Feb. 22, 2016", 9 pgs.

"U.S. Appl. No. 13/841,405, Response filed Jul. 23, 2015 to Non Final Office Action dated Apr. 23, 2015", 12 pgs.

"U.S. Appl. No. 13/841,405, Response filed Oct. 17, 2014 to Restriction Requirement dated Sep. 11, 2014", 7 pgs.

"U.S. Appl. No. 13/841,405, Response filed Dec. 28, 2015 to Final Office Action dated Oct. 1, 2015", 14 pgs.

"U.S. Appl. No. 13/841,405, Restriction Requirement dated Sep. 11, 2014", 7 pgs.

"U.S. Appl. No. 13/841,405, Resubmitted Response Filed Feb. 3, 2016 to Final Office Action dated Oct. 1, 2015", 14 pgs.

"U.S. Appl. No. 15/160,373, Non Final Office Action dated Mar. 14, 2018", 10 pgs.

"U.S. Appl. No. 15/160,373, Notice of Allowance dated Nov. 20, 2018", 8 pgs.

"U.S. Appl. No. 15/160,373, Response Filed Jul. 13, 2018 to Non-Final Office Action dated Mar. 14, 2018", 9 pgs.

"Application Serial No. 16/270,223, Preliminary Amendment filed Feb. 8, 2019", 7 pgs.

"European Application Serial No. 14763415.8, Extended European Search Report dated Nov. 7, 2016", 7 pgs.

"European Application Serial No. 14763415.8, Response filed Jun. 6, 2017 to Extended European Search Report dated Nov. 7, 2016", 8 pgs.

"International Application Serial No. PCT/US2014/028610, International Preliminary Report on Patentability dated Sep. 24, 2015", 10 pgs.

"International Application Serial No. PCT/US2014/028610, International Search Report dated Jul. 24, 2014", 4 pgs.

"International Application Serial No. PCT/US2014/028610, Written Opinion dated Jul. 24, 2014", 8 pgs.

Sloan, Robert, "CD Horizon Voyager, Mini-Open Rod System, Surgical Technique", Medtronic, (2012), 36 pgs.

"U.S. Appl. No. 16/270,223, Corrected Notice of Allowability dated Aug. 4, 2021", 3 pgs.

"Canadian Application Serial No. 3,065,039, Response filed Jul. 16, 2021 to Office Action dated Mar. 24, 2021", 26 pgs.

"European Application Serial No. 14763415.8, Response filed Oct. 20, 2021 to Communication Pursuant to Article 94(3) EPC dated Jun. 10, 2021", 27 pgs.

\* cited by examiner

US 11,484,350 B2

SPLIT TOWER FOR A BONE ANCHOR

CLAIM OF PRIORITY

This application claims the benefit of U.S. Provisional Patent Application Ser. No. 62/779,255, filed on Dec. 13, 2018, the benefit of priority of which is claimed hereby, and which is incorporated by reference herein in its entirety.

BACKGROUND

Orthopedic devices such as rods, plates, tethers, staples, and other devices can be used in various spinal procedures to correct abnormalities (e.g., scoliosis) or to address injuries (e.g., vertebral fracture). In some spinal procedures, anchors and rods can be secured along a spinal column between one or more vertebrae to stabilize a region of the spine. Some surgical procedures performed on the spinal column using such devices have become less invasive. However, some special parts used in minimally-invasive spinal procedures can increase the difficulty of the installation procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
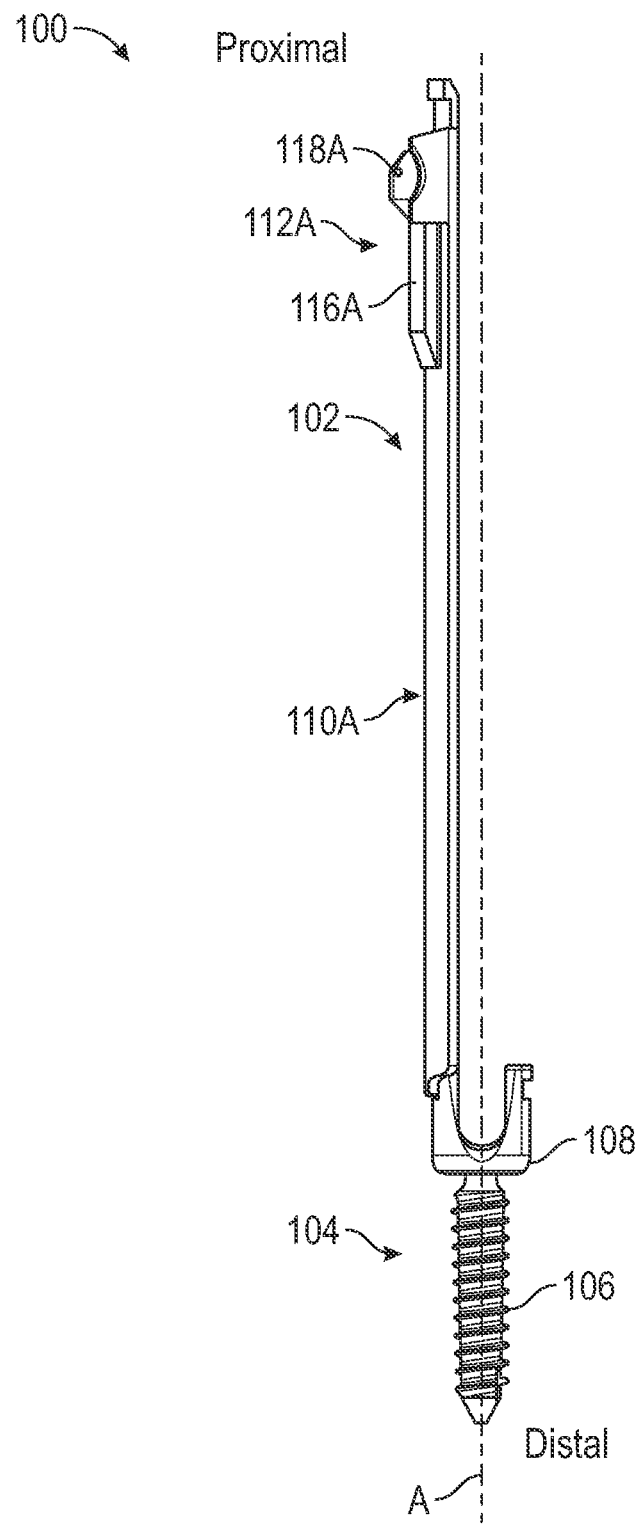
FIG. 1A illustrates a front view of a tower assembly in a first condition, in accordance with at least one example of this disclosure.

Bone anchors can be used together with connecting members (such as rigid and semi-rigid rods) to straighten a region of a human spine to address a spinal abnormality (e.g., scoliosis), to stabilize a spine following an injury (e.g., fractured vertebrae), or to address degeneration of the spine caused by disease. In minimally invasive spinal procedures to address these issues, multiple small incisions can be made to form multiple small cavities near individual vertebrae. A large amount of the procedure can be performed through manipulation of instruments and components extending through the small surgical cavities using special instruments that are able to be manipulated from outside of the cavities.

For example, anchors are commonly driven into vertebrae, where the anchors include extensions coupled to the anchors and where the extensions have a length sufficient to extend outside of the cavity so that the anchors (and components engaging the anchors) can be manipulated from outside of the cavities. In some of these devices, extended tabs of the anchors can be used to extend through the cavities, which often must be separable from the heads of the anchors (which remain secured to vertebrae). Further, because the extensions often need to receive a connecting member and a closure top (or set screw), the extensions must often be of a quantity of at least two to allow threading of the closure top into the head of the anchor and to provide a slot to reduce and retain the connecting member.

Some designs include two extensions each coupled to the head of the anchor at a breakaway portion, where each extended tab can be individually bent to allow separation of the extension from the head at the breakaway portions. This design requires relative movement of the extended tabs for separation. However, the extended tabs must also be rigid enough to transfer forces between the tabs and the head. For example, sometimes forces must be transferred from a portion of the extended tabs external to the cavity to a portion of the extended tabs into the cavity and ultimately to the head and/or shank of the anchor. However, such operations can cause undesired separation of the extension or extended tab from the anchor, which can increase a risk of material being lost into a cavity and can add another step to the procedure.

Other designs include towers that are releasably connected to the anchors. Many of these designs are connected to the anchor at an angle. Some of these designs also require a single-piece assembly including a rigid and closed top, which can obstruct vision down the anchor and into the cavity during an operation. This disclosure addresses problems with existing towers and extended tab designs by providing a split tower assembly that is releasably securable to a head or housing of the anchor. The split tower can be sufficiently rigid to allow for transfer of forces from the tower external to an opening and down to an anchor while limiting unwanted separation from the anchor.

Because of the tower assembly's split design and quick, separable locking mechanism, the tower can be relatively quickly removable from the anchor to allow the tower assembly to be easily removed from the opening following use of the tower for reduction (for example). Because a cap of the tower can be easily removed at any time, the tower can help improve visualization of components within the opening (e.g., anchor, connecting rod, and/or set screw) during the operation.

Also, by providing a relatively straight split tower assembly, the tower assembly can help to reduce stretching of the surgical site. And, because the tower assembly can be removed straight out of an opening (for example, without significant side to side movement for breaking an extended tab), stretching can be further reduced.

Figure 1B:
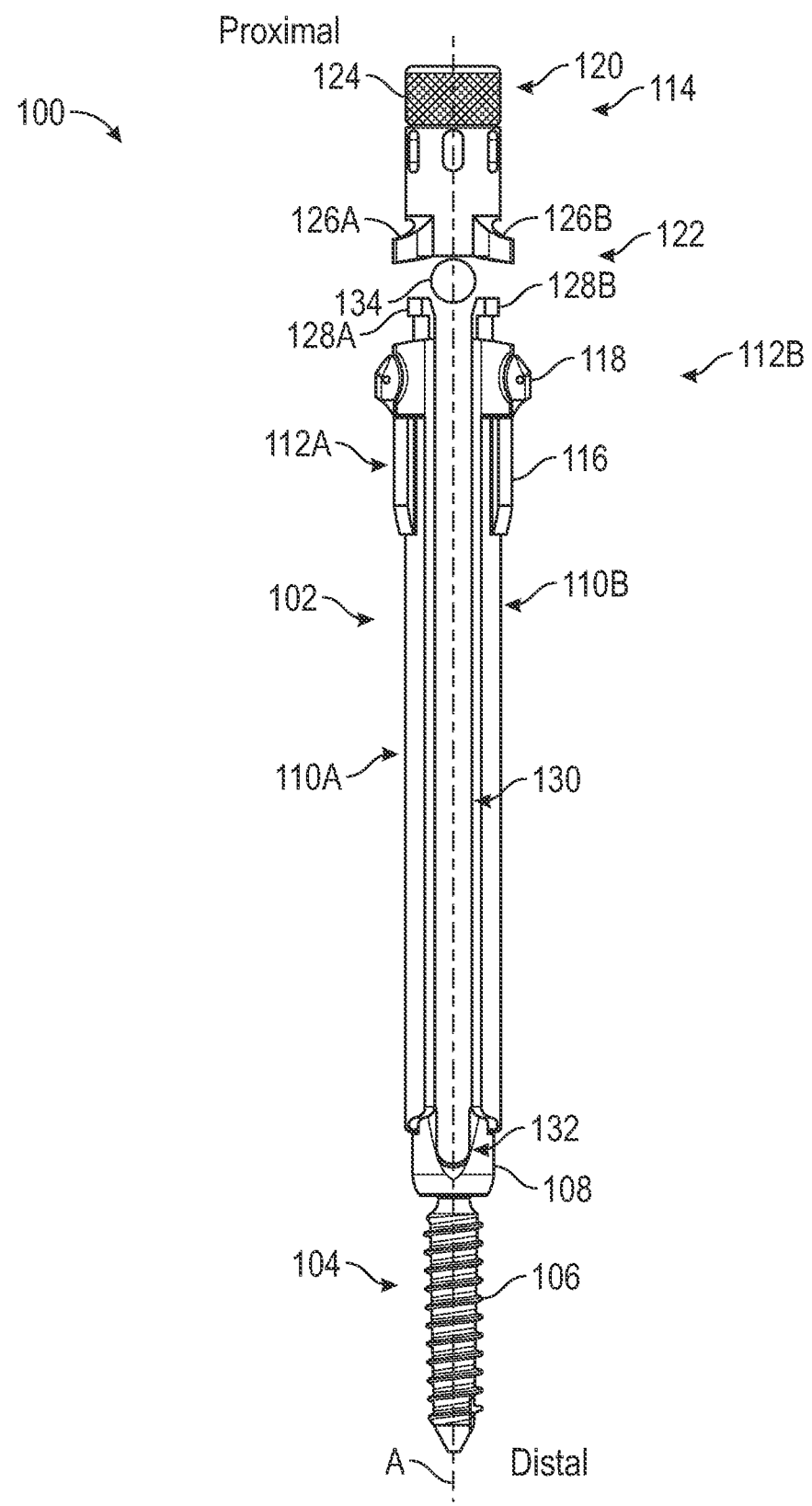
FIG. 1B illustrates a front view of a tower assembly in a second condition, in accordance with at least one example of this disclosure.
Figure 1C:
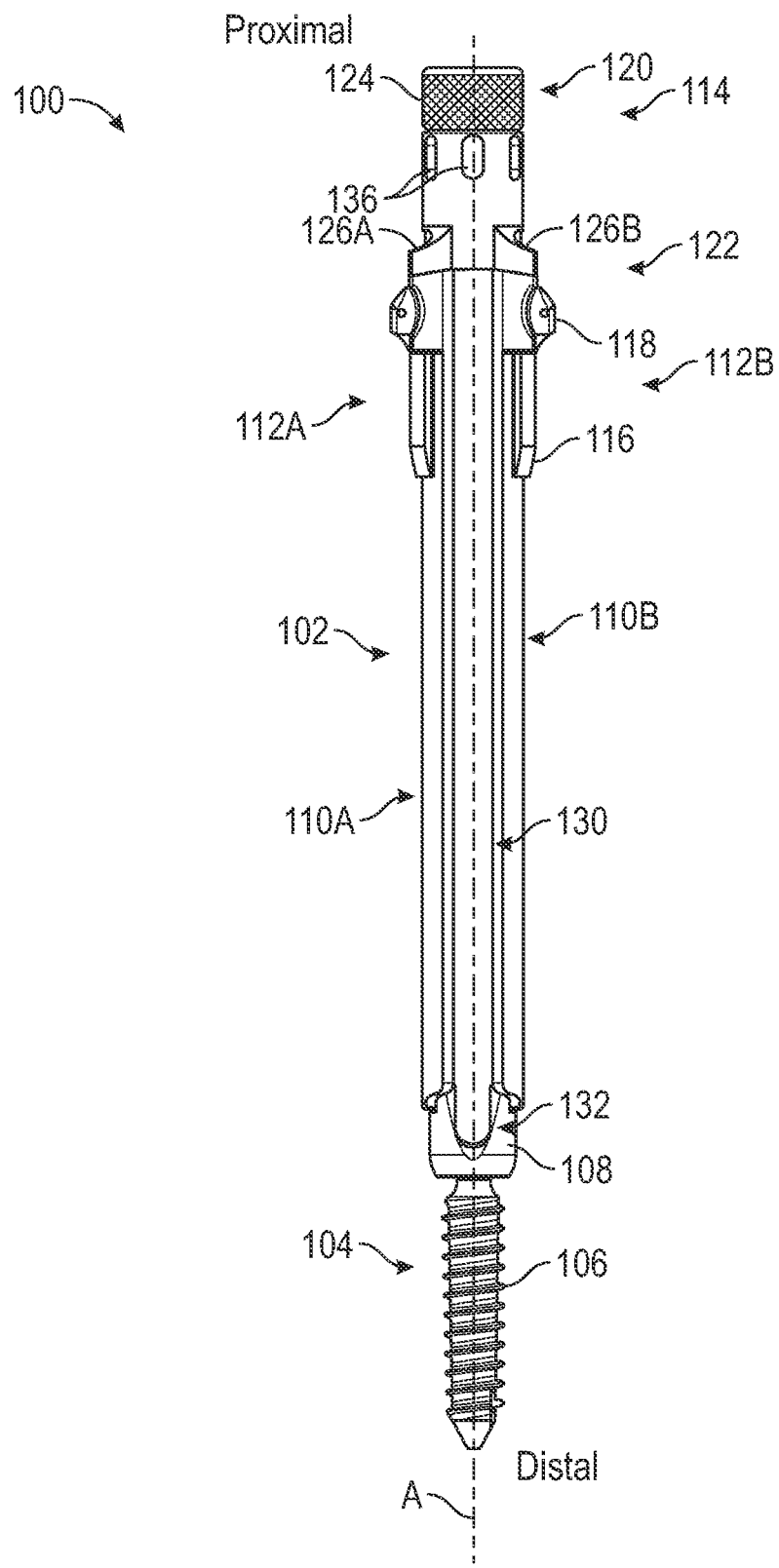
FIG. 1C illustrates a front view of a tower assembly in a third condition, in accordance with at least one example of this disclosure.

FIG. 1A illustrates a front view of a tower assembly 100 in a first condition, in accordance with at least one example of this disclosure. FIG. 1B illustrates a front view of the tower assembly 100 in a second condition, in accordance with at least one example of this disclosure. FIG. 1C illustrates a front view of the tower assembly 100 in a third condition, in accordance with at least one example of this disclosure. FIGS. 1A-1C are discussed below concurrently.

The tower assembly 100 can include a tower 102 and an anchor 104. The anchor 104 can include a shank 106, and a head or housing 108. The tower 102 can include arms 110A and 110B (collectively referred to as arms 110), locks 112A and 112B (collective referred to as locks 112), and a cap 114. Each lock 112 can include a lever 116 and a cam 118. The cap 114 can include a proximal portion 120 and a distal portion 122. The proximal portion 120 can include a knob 124. The distal portion 122 can include eyes 126A and 126B. Each of the arms 110 can include a proximal projection 128 (128A and 128B) (shown in FIGS. 1B and 1C). The arms 110 can form channels 130 and the head 104 can form channels 132. Also shown in FIGS. 1A-1C are axis A and orientation indicators Proximal and Distal. Also shown in FIG. 1B is a connecting member 134.

Each component of the tower 102 and the anchor 104 can be comprised of rigid and semi-rigid materials such as metals, plastics, composites, or the like. In some examples, the tower 102 and/or the anchor 104 can be comprised of bio-compatible materials, such as stainless steel, titanium, or the like. In some examples, the tower 102 and/or the anchor 104 can be comprised of only one material, and can be comprised of multiple materials in other examples.

The head 108 of the anchor 104 can be coupled to the shank 106 at a distal portion of the head 108 with the shank 106 extending distally therefrom and where the axis A can be a central axis for the head 108 and the shank 106. In other examples, the shank 106 can deviate from the axis A at various angles. The shank 106 can be a threaded shank or screw including male threads configured to engage bone, such as a relatively coarse thread pattern. The head 108 of the anchor 104 can form the channels 132, which can be generally U-shaped channels alignable with the channels 130 of the arms 110, which can each be configured to receive the connecting member 134 therethrough.

In some examples, the shank 106 can be configured to threadably secure to a vertebra of a spine of a human. The shank 106 can be an integral component to the head 110 in some examples, coupled to a distal portion of the head 110. In other examples, the shank 160 can be a portion of a fastener that is a separate component from the head 110 and can be disposed within a bore of the head 110 and configured to be retained therein.

The arms 110A and 110B can be generally elongate members extending substantially parallel to axis A when coupled to the head 108 of the anchor 104. As discussed below in further detail, each of the arms 110 can include an inner sleeve and an outer sleeve, where the sleeves can be translated relatively to lock the arms 110 to the head 108 individually at a distal portion of each of the arms 110. Together the arms 110 can define the channels 130, which can align with the channels 132 of the head 108 of the anchor 104 when the arms 110 are secured to the anchor 104. In some examples, the channels 130 and 132 can be configured to receive the connecting member 134 therethrough. The proximal projections 128 can be projections extending radially outward from the inner sleeve of the arms 110 and can be sized and shaped to couple to the eyes 126 of the distal portion 122 of the cap 114.

The locks 112A and 112B can be secured to a proximal portion each the arms 110A and 110B, respectively. For example, the lever 116A can be secured to the cam 118A, where the cam 118A can be coupled to a proximal portion of the arm 110A. As discussed below, the levers 118 can be operable to move the cams 116 to individually lock and unlock the arms 110 to the head 108 of the anchor 108.

The knob 124 can be an actuator coupled to the proximal portion of the cap 114. The knob 124 can be knurled in some examples, and can have other surface finishes to improve grip (such as milling textures). The distal portion 122 can include eyes 126A and 126B, which can be openings in the distal portion 122. The knob 124 can be coupled to a threaded piston within the cap 114 and the knob 124 can be rotatable relative to the cap 114 to translate the piston with respect to the cap 114 and the knob 124. Also shown on the cap 114 are tool bores 136, which can be bores in a body of the cap 114 configured to receive a portion of a tool therein for mounting of the tool to the cap 114.

In operation of some examples, the distal portion of the arm 110A can be secured to the head 108 by engaging the distal portion of the arm 110A with the head 108 and by operating the lock 112A to secure the arm 110A to the anchor 104, as shown in FIG. 1A. In some examples, the arm 110A can be secured to the head 108 before the tower assembly 100 is inserted into an opening. In other examples, the arm 110A can be secured to the head 108 after the shank 106 is secured to a bone of a patient.

After securing a first of the arms 110, a second arm can be secured to the anchor 104. For example, the distal portion of the arm 110B can be secured to the head 108 by engaging the distal portion of the arm 110B with the head 108 and by operating the lock 112B to secure the arm 110B to the anchor 104, as shown in FIG. 1B. In some examples, the tower 102 and anchor 104 can be inserted into an opening of a patient following securing of the arms 110 to the head 108. Because the channels 130 are open from a proximal perspective, the tower assembly can help provide relatively easy insertion of tools into the head 108 and can provide an improved viewing perspective. In some examples, after securing the arms 110 to the anchor, the arms 110 (or the channels 130 of the arms 110) can be used to guide the connecting member 134 into the channels 130 and into the channels 132 of the anchor 104. In other examples, the tower 102 can be inserted into a cavity before the connecting member is inserted into the channels 130.

Once the arms 110 are secured to the anchor 104, the cap 114 can be secured to the arms 110. The proximal projections 128A and 128B can be inserted into a distal opening of the cap 114 until a distal portion of the cap 114 contacts a proximal portion of the outer sleeve. The knob 124 can then be rotated (for example in a clock-wise direction about axis A from a proximal perspective) to translate the piston within the cap 114 distally. The piston can engage a radially inner portion of the proximal projections 128A and 128B to force the proximal projections 128A and 128B radially outward into the eyes 126A and 126B. The piston can thereby prevent radially inward movement of the proximal projections 128A and 128B with respect to the cap 114 when the piston is translated distally. In such a position, the proximal projections 128A and 128B can contact the eyes 126A and 126B, respectively, to limit translation of the arms 110 with respect to the cap 114, securing the arms 110A and 110B to each other and to the cap 114, and helping to transfer forces between the head 108, the arms 110, and the cap 114. Because the levers 116 can be operated to lock the arms 110 to the head 108 by hand and because the knob 124 can be operated to secure the cap 114 to the arms 110 by hand, the tower 102 can be secured to the head 108 without additional or specialized tooling.

In some examples, the connecting member 134 can be inserted into the channel 130 and translated distally into the channel 132 of the head 108 following securing of the cap 114 to the arms 110. In some examples, the shank 106 can be secured to a bone of a patient before or after any of the steps discussed above. In further examples, the arms 110 can be used to apply a force on the anchor 102 to manipulate a position of the bone of the patient, such as during a de-rotation procedure.

Once the connection member 134 and shank 106 are in place, a set screw can be inserted into the channel 130 and can be secured to the channels 132 of the head 108 to retain the connecting member 134 within the head 108. In some examples, the connection member 134 can be reduced (or forced) distally by the set screw from the channels 130 of the arms 110 into the channels 132 of the head 108. During such a process, the cap 114 can help prevent separation or splaying of the arms 110.

After the anchor 104 is positioned as desired, the tower 102 can be removed by reversing the steps discussed above. The knob 124 can be rotated counter-clockwise to release the proximal projections 128 from the cap 114 and the cap 114 can be removed from the arms 110. The lock 112B can then be operated to unlock the distal portion of the arm 110B from the head 108 and the arm 110B can be separated from the head 108 and removed from the opening. The lock 112A can then be operated to unlock the distal portion of the arm 110A from the head 108 and the arm 110A can be separated from the head 108 and removed from the opening. The arms 110 can be removed in any order. In some examples, the anchor 104 can be manipulated using only one of the arms 110. In some examples, a single arm, such as the arm 110A, can be used to guide reduction of the connection member 134 and/or the set screw.

Figure 2:
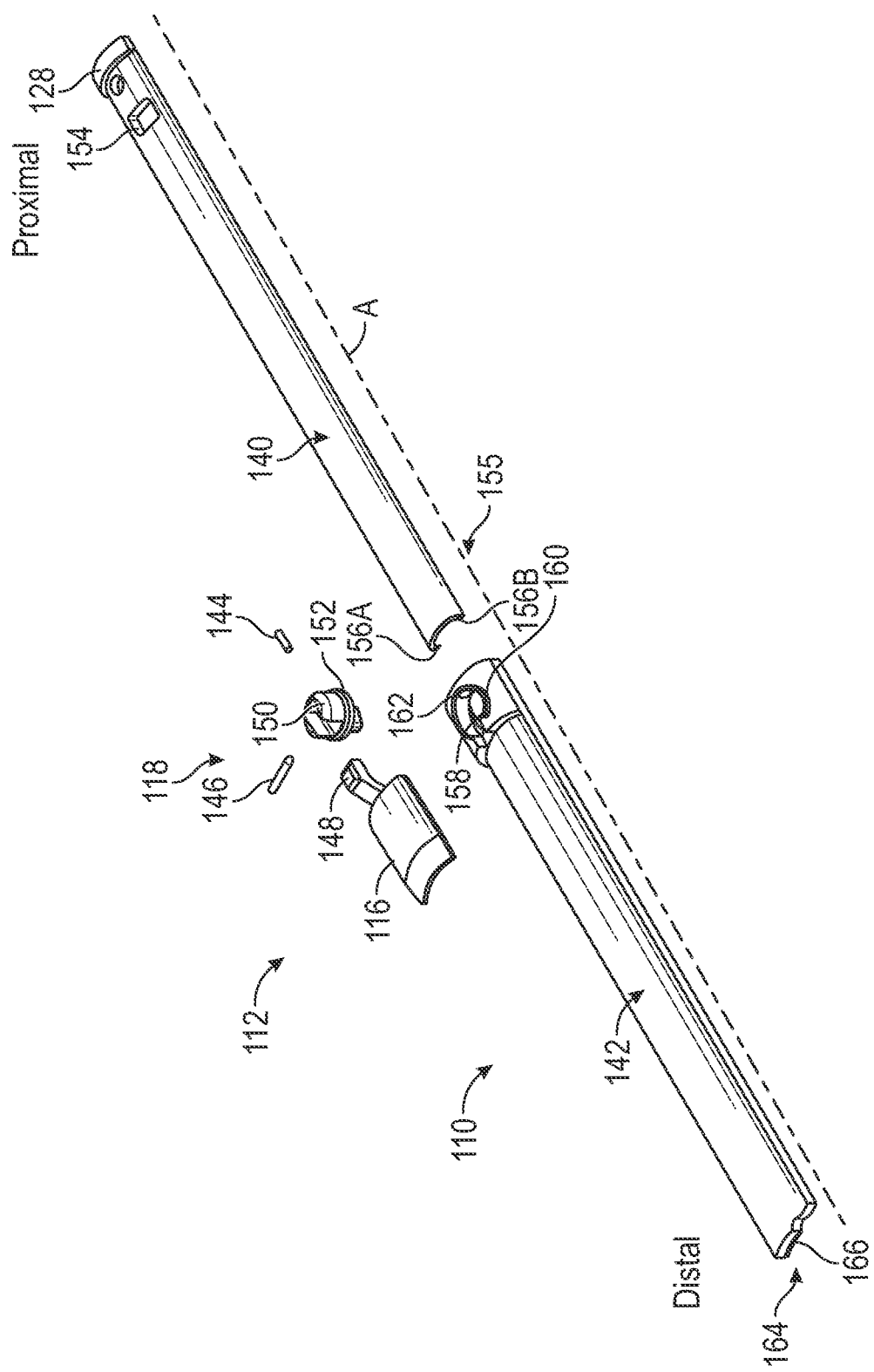
FIG. 2 illustrates an exploded isometric view of an anchor assembly, in accordance with at least one example of this disclosure.

FIG. 2 illustrates an exploded isometric view the anchor assembly 100, in accordance with at least one example of this disclosure. The anchor assembly 100 can include the arm 110 and the lock 112. The arm 110 can include an inner sleeve 140 and an outer sleeve 142. The lock 112 can include the lever 116, the cam 118, a cam pin 144, and a lever pin 146. The lever 116 can include a lever pin bore 148, and the cam 118 can include cam pin bores 150, and a cam pin groove 152. The inner sleeve 140 can include a projection bore 154 and a distal portion 155 of the inner sleeve 140 can include distal projections 156A and 156B. The outer sleeve 142 can include a cam bore 158, a collar 160, a sleeve pin bore 162, and a distal portion 164 including a distal hook 166.

The cam pin 144 and the lever pin 146 can be rigid or semi-rigid fasteners configured to secured the lever 116 to the cam 118 and the cam 118 to the outer sleeve 142, respectively. In some examples, the cam pin 144 and the lever pin 146 can be pins, but can be other types of fasteners, such as screws or bolts, in other examples.

The cam bore 158 can be a bore in the collar 160 of the outer sleeve 142, where the cam bore 158 extends through the outer sleeve 142 substantially orthogonally to the axis A. The sleeve pin bore 162 can intersect with the cam bore 158 and can be sized to receive the cam pin 144 therein. The lever pin bore 148 can be a bore extending through a head of the lever 116 and configured to receive the lever pin 146 therethrough. Similarly, the cam pin bores 150 can be bores extending through the cam 118. The cam pin groove 152 can be a groove extending around a part of a circumference of the cam 118 and configured to receive and retain a portion of the cam pin 144 therein. The projection bore 154 can be a bore extending through the inner sleeve 154 proximate a proximal portion of the inner sleeve 140.

In assembly of some examples, the inner sleeve 140 and the outer sleeve 142, can each extend along the axis A. In some examples, the inner sleeve 140 can be inserted into the outer sleeve 142 until the projection bore 154 at least partially aligns with the cam bore 162. The cam 118 can then be inserted into the cam bore 158 of the collar 160 of the outer sleeve 142 such that a projection of the cam 118 extends into the projection bore 154. The cam pin 144 can then be inserted through the sleeve pin bore 162 and partially into the cam pin groove 152 to retain the cam 118 within the cam bore 158.

Either before or after the cam 118 is secured to the outer sleeve, a head of the lever 116 can be inserted into a notch in the cam 118 and the lever pin 146 can be inserted into the cam pin bore 150 and the lever pin bore 148 to secure the lever 116 to the cam 118 and therefore to the outer sleeve 142.

The distal projections 156A and 156B can be projections extending distally from the distal portion 155 of the inner sleeve 140. In some examples, the distal projections 156A and 156B can be kidney-shaped, bean-shaped, oval-shaped, or the like. The distal hook 166 of the distal portion 164 can be a hook extending distally and radially inward from the distal portion 164 of the outer sleeve 142. The distal projections 156A and 156B and the distal hook 166 are discussed further below with respect to FIGS. 3A-3E.

Figure 3A:
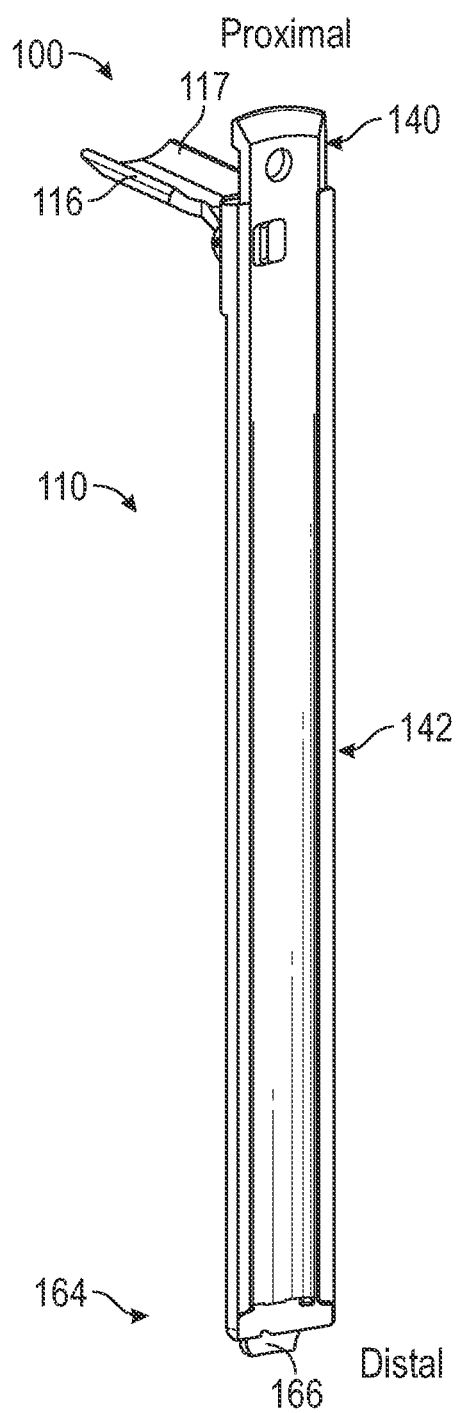
FIG. 3A illustrates an isometric view of a tower assembly in a first condition, in accordance with at least one example of this disclosure.
Figure 3B:
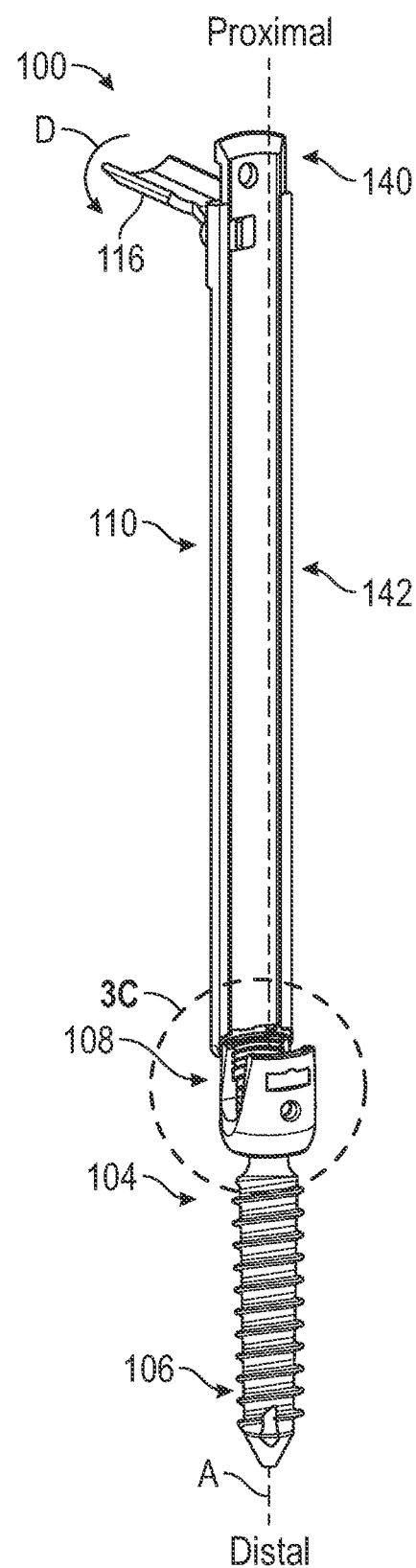
FIG. 3B illustrates an isometric view of a tower assembly in a second condition, in accordance with at least one example of this disclosure.
Figure 3C:
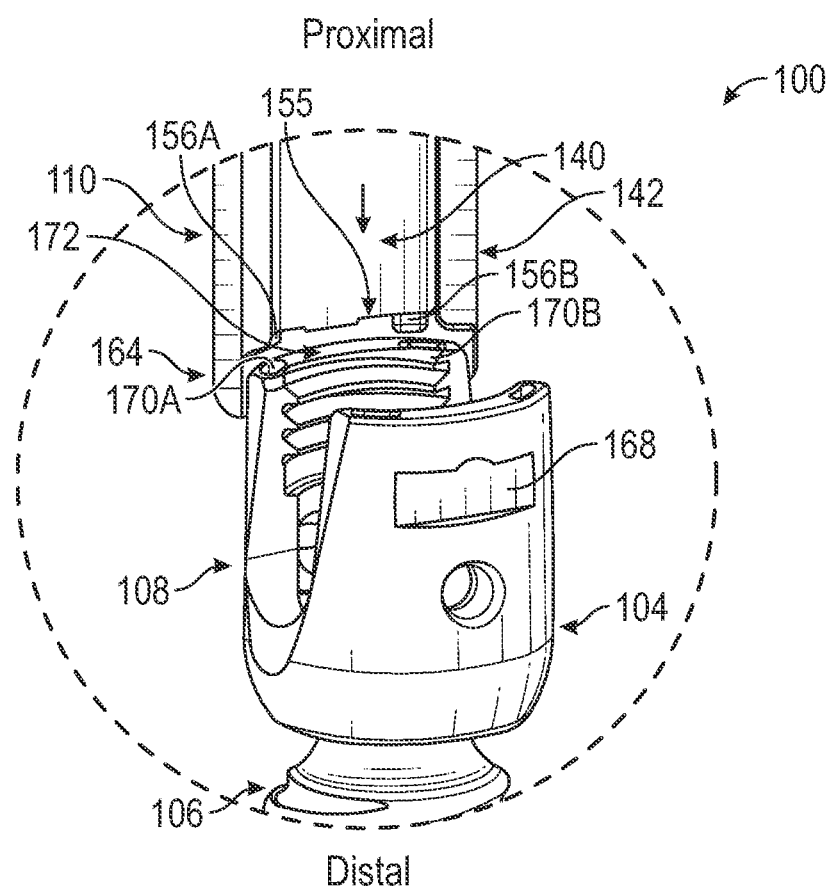
FIG. 3C illustrates a focused isometric view of a tower assembly in a second condition, in accordance with at least one example of this disclosure.
Figure 3D:
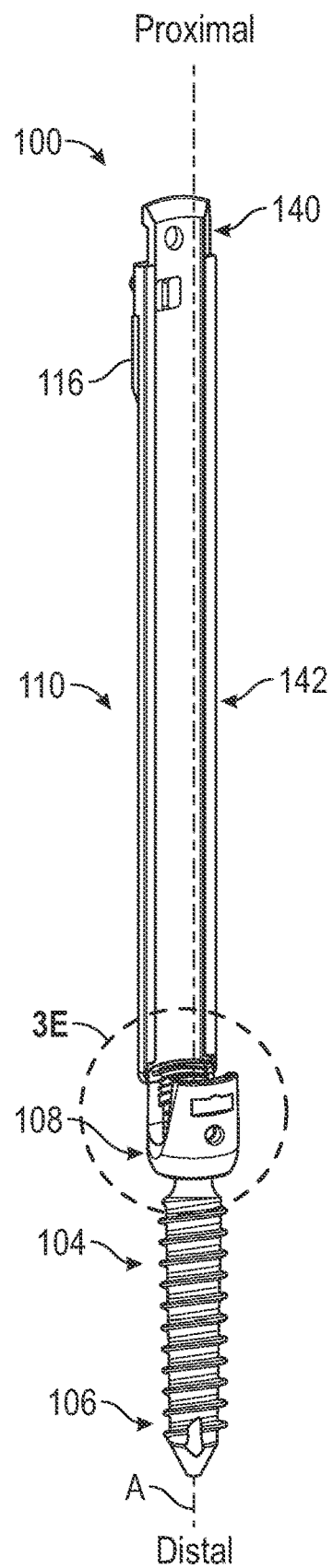
FIG. 3D illustrates an isometric view of a tower assembly in a third condition, in accordance with at least one example of this disclosure.
Figure 3E:
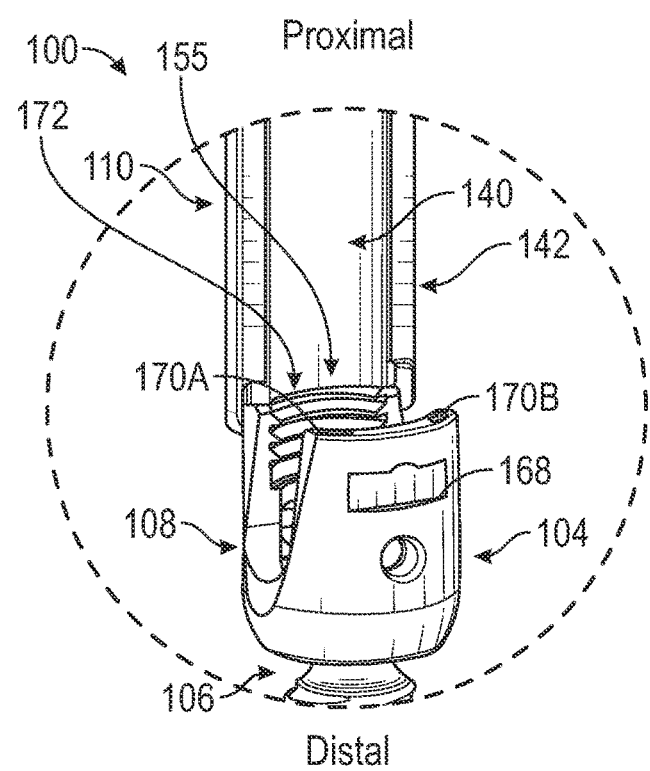
FIG. 3E illustrates a focused isometric view of a tower assembly in a third condition, in accordance with at least one example of this disclosure.

FIG. 3A illustrates an isometric view of the tower assembly 100 in a first condition, in accordance with at least one example of this disclosure. FIG. 3B illustrates an isometric view of the tower assembly 100 in a second condition, in accordance with at least one example of this disclosure. FIG. 3C illustrates a focused isometric view of the tower assembly 100 in a second condition indicated by indicator 3C of FIG. 3B, in accordance with at least one example of this disclosure. FIG. 3D illustrates an isometric view of the tower assembly 100 in a third condition, in accordance with at least one example of this disclosure. FIG. 3E illustrates a focused isometric view of the tower assembly 100 in a third condition indicated by indicator 3E of FIG. 3D, in accordance with at least one example of this disclosure. FIGS. 3A-3E are discussed below concurrently.

The components of the tower assembly 100 can be consistent with FIGS. 1A-2 above; FIGS. 3A-3E show additional details of, and interactions between, the components of the tower assembly 100. For example, FIG. 3A shows lever 116 in an unlocked position and shows an internal surface 117 of the lever 116, where the internal surface 117 can be shaped to match an outer surface of the outer sleeve 142 so that the lever 116 can rest against the outer surface of the outer sleeve 142. Also, a periphery of the lever 116 can have a reduced thickness to help allow the lever 116 to be grasped when the lever is in the locked position and resting on the outer sleeve 142.

FIG. 3B shows the lever 116 in the unlocked position, but shows the distal hook 166 engaged with a slot 168 of the head 108 of the anchor 104. In some examples, the slot 168 can be a channel or slot extending radially into the head 108 of the anchor. The slot 168 can be sized to receive the distal hook 166 therein and can include proximal and distal flats configured to contact the distal hook 166 to help prevent axial translation of the arm 110 with respect to the head 108. In some examples, the inner sleeve 140 and/or the outer sleeve 142 can have a radius of curvature configured to mate with an outer surface of the head 108.

FIGS. 3B and 3C also show distal projections 156A and 156B, which can be aligned with proximal bores 170A and 170B, respectively, when the hook 166 is secured to one of the channels 168 of the head 108. The proximal bores 170A and 170B can extend into a proximal portion 172 from a proximal surface of the head 108. The proximal bores 170A and 170B can be sized and shaped complimentary to the distal projections 156A and 156B. That is, the proximal bores 170A and 170B can be oval-shaped, bean-shaped, kidney-shaped, or the like.

FIGS. 3D and 3E shows the tower assembly 100 in a third condition where the distal hook 166 remains inserted into or engaged with the channel 168 of the head 108 of the anchor 104. When the inner sleeve is translated distally by rotating the lever 116 in a direction D (shown in FIG. 3B), the distal projections 156A and 156B are translated into the proximal bores 170A and 170B, and the distal portion 155 of the inner sleeve 140 can be in contact with the proximal portion 172 of the head 108. Because the distal hook 166 can apply a distal-to-proximal force on the head 108 and because the distal portion 155 can provide a proximal-to-distal force on the proximal portion 172 of the head 108, the head 108 is pinched by the inner sleeve 140 and the outer sleeve 142, helping to prevent proximal and distal translation of the arm 110 with respect to the head 108.

Further, because the distal projections 156A and 156B are disposed in the proximal bores 170A and 170E when the inner sleeve is translated distally, the sleeve 110 is substantially prevented from moving radially (or non-axially) with respect to the head 108. This arrangement can help prevent the arm 110 from unintentionally separating from the head 108.

Though the example above is discussed as including the channel 168 to receive the distal hook 166, the tower assembly 100 can be configured to connect to any screw or fastener including a ledge, shelf, or bore. For example, the distal hook 166 can be configured to retain a standard screw head in some examples. In some examples, the arms 110 can include additional projections or hooks to engage additional bores or grooves on a fastener to help reduce rotation of the fastener with respect to the arms 110.

Figure 4A:
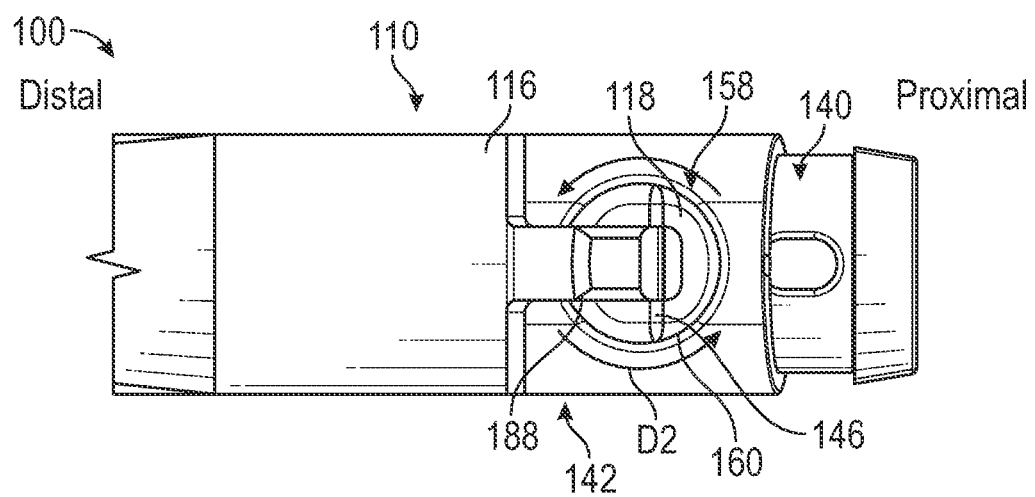
FIG. 4A illustrates a side view of a portion of a tower assembly, in accordance with at least one example of this disclosure.
Figure 4B:
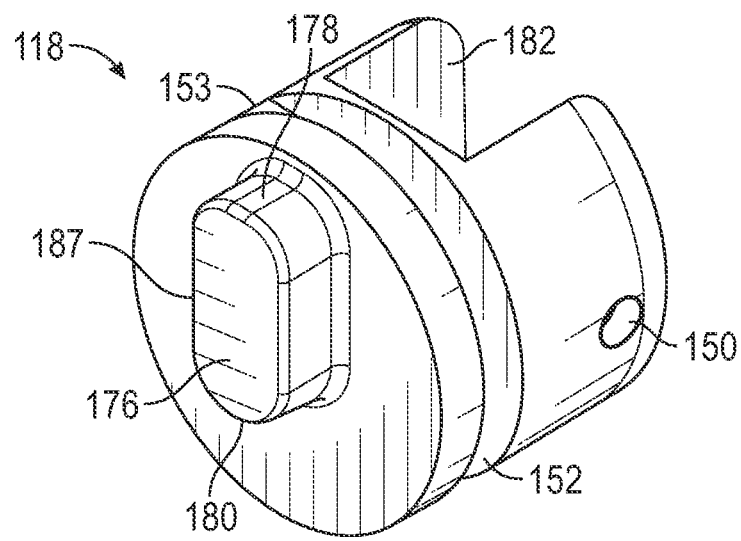
FIG. 4B illustrates an isometric view of a portion of a tower assembly, in accordance with at least one example of this disclosure.
Figure 4C:
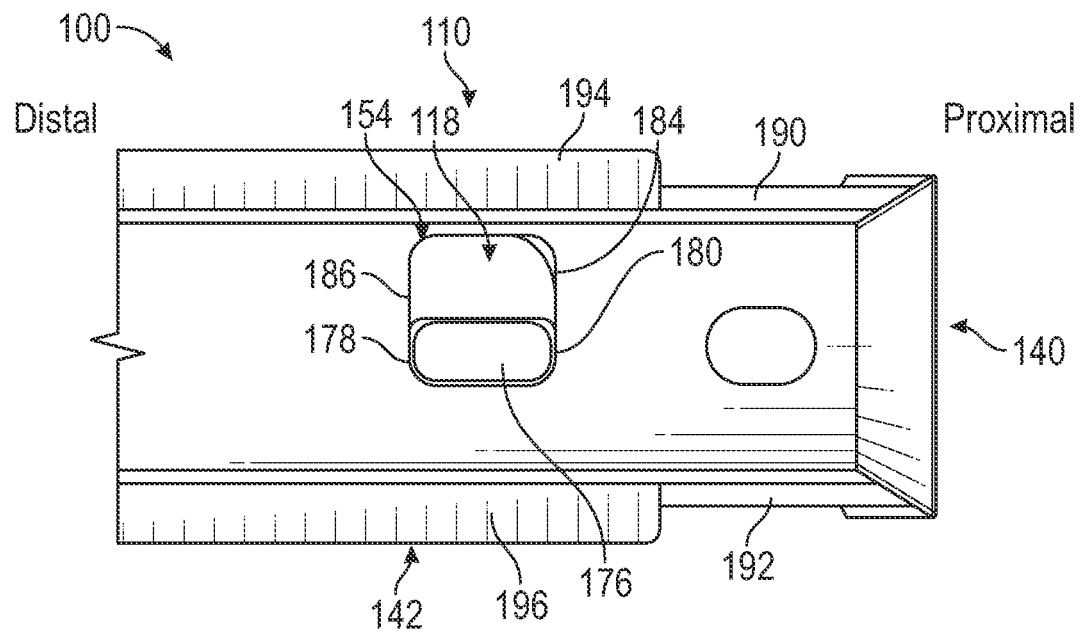
FIG. 4C illustrates a focused rear view of a tower assembly in a first condition, in accordance with at least one example of this disclosure.
Figure 4D:
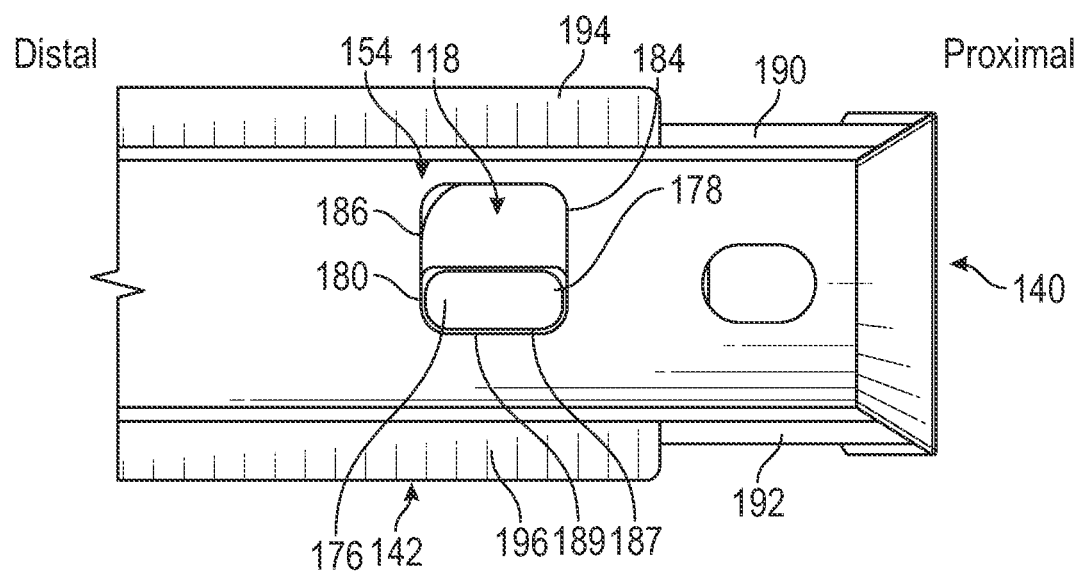
FIG. 4D illustrates a focused rear view of a tower assembly in a second condition, in accordance with at least one example of this disclosure.

FIG. 4A illustrates a side view of a portion of the tower assembly 100, in accordance with at least one example of this disclosure. FIG. 4B illustrates an isometric view of the cam 118, in accordance with at least one example of this disclosure. FIG. 4C illustrates a focused rear view of the tower assembly 100 in a first condition, in accordance with at least one example of this disclosure. FIG. 4D illustrates a focused rear view of the tower assembly 100 in a second condition, in accordance with at least one example of this disclosure. FIGS. 4A-4D are discussed below concurrently.

The components of the tower assembly 100 shown in FIGS. 4A-4D can be consistent with those discussed above with respect to FIGS. 1A-3E; FIGS. 4A-4D show additional details of the tower assembly 100. For example, FIG. 3A shows cam 118 disposed within the cam bore 158 of the collar 160 of the outer sleeve 142. FIG. 3A also shows the cam pin 146 securing the cam 118 to the collar 160.

FIG. 4B shows a projection 176 of the cam 118, which can have a generally oval shape, elliptical shape, rounded rectangular prism shape, or the like. The projection 176 can be a boss, in some examples, extending from a surface of the cam 118 substantially orthogonally to the axis A when the cam is inserted into the bore 158 of the collar 160. In some examples, the projection 176 can have an inner side 178 and an outer side 180. In some examples, the inner side 178 and the outer side 180 can have the same geometry. In other examples, the outer side 178 can be different from the inner side 180, such as a relatively flatter shape to help limit accidental rotation of the cam 118.

FIG. 4B also shows the pin channel 152 of the cam 118, which can extend around most of a circumference of the cam 118, but can terminate at pin stop 153. The pin stop 153 can be configured to contact the cam pin 144 to limit rotation of the cam 118 relative to the outer sleeve 142. The cam 118 can include a second pin stop to limit rotation of the cam 118 in a second rotational direction.

FIG. 4B further shows a lever notch 182, which can be a notch sized and shaped to receive a head of the lever 116. The cam pin bore 150 can intersect with the lever notch 182 so that the lever pin bore 148 can receive the lever pin 146 therethrough to secure the lever 116 to the cam 118. The lever notch 182 can also be sized and shaped to allow the lever 116 to rotate about the lever pin 146 with respect to the cam 118.

FIGS. 4C and 4D show how the cam 118, the inner sleeve 140, and the outer sleeve 142 work together to translate the inner sleeve 140. The projection bore 154 can include a proximal wall 184 and a distal wall 186. In operation of some examples, when the lever 116 is in the unlocked position (as shown in FIGS. 3A and 3B the projection 176 can be oriented in a proximal position such that the outer surface 180 of the projection 176 rests against the proximal wall 184 and the inner surface 178 rests against the distal wall 186 of the projection bore 154.

The lever 116 can then be rotated as indicated by direction D of FIG. 3B causing the cam 118 to rotate counterclockwise with respect to FIGS. 4C and 4D. During rotation of the cam 118, the projection 176 also rotates with respect to the inner sleeve 140 and the outer sleeve 142. During rotation, the projection 176 contacts the walls of the projection bore 154, causing the inner sleeve 140 to translate distally as the cam is rotated 180 degrees until a side wall 187 of the projection 176 contacts a wall 189 of the projection bore 154. In some examples, the cam pin 144 can contact the pin stop 153 to help limit rotation of the cam 118. Once the cam 118 can no longer rotate, the lever 116 can be pressed down toward the outer sleeve 142.

In such an arrangement, the projection 176 can be compressed inward at the outer surface 180 and the inner surface 178 by the inner sleeve 140 to create a friction fit between the inner sleeve 140 and the projection 176 to help prevent accidental rotation of the cam 118 with respect to the sleeve. In some examples, a side wall 187 of the projection 176 and a side wall 189 of the projection bore 154 can both engage in the locked position to create a flat-to-flat engagement to limit accidental rotation of the cam 118.

When the lever 116 is pivoted downward to rest against the outer arm, a neck or head of the lever 116 can be engaged with a notch 188 of the collar 160. Engagement of the lever 116 and the notch 188 of the collar 160 can help limit rotation of the cam 118 with respect to the outer sleeve 142 when the lever 116 is in the downward or locked position to help prevent accidental unlocking of the arm 110 from the head 108.

When it is desired to unlock the arm 110 from the head 108, the lever 116 can be lifted off the arm 110 by pivoting the lever about the lever pin 146. The lever 116 can then be rotated to cause rotation of the cam 118 to move the projection 176 in a clock-wise rotational direction with respect to FIGS. 4C and 4D to translate the inner sleeve 140 proximally with respect to the outer sleeve 142. Such a process can be repeated as desired.

FIGS. 4C and 4D also show chamfers 190 and 192 of the inner sleeve 140. The chamfers 190 and 192 can be chamfered edges extending parallel with longitudinal axis of the inner sleeve 140. The outer sleeve 142 can include a pair of opposing rails 194 and 196 configured to receive the chamfers 190 and 192 therein to create a sliding engagement between the inner sleeve 140 and the outer sleeve 142. The engagement between the chamfers 190 and 192 and the rails 194 and 196 can help to guide translation and prevent non-translation movement of the inner sleeve 140 within the outer sleeve 142.

Though FIGS. 4A-4D describe the lock 112 as including cam 118 as being operable to translate the inner sleeve 140 with respect to the outer sleeve 142, other examples can include other components that can perform such operations. For example, the lock 112 can include a worm drive engageable with one or both of the inner sleeve 140 and the outer sleeve 142 where the worm drive can be rotatable to translate the inner sleeve 140 with respect to the outer sleeve 142. In other similar examples, other gears can be used. In other examples, the lock 112 can include a biasing element, such as a spring, to bias the inner sleeve 140 with respect to the outer sleeve 142. In further examples, the lock can include a collar or ring to engage a threaded portion of one of the sleeves to cause the inner sleeve 140 to translate with respect to the outer sleeve 142.

Figure 5:
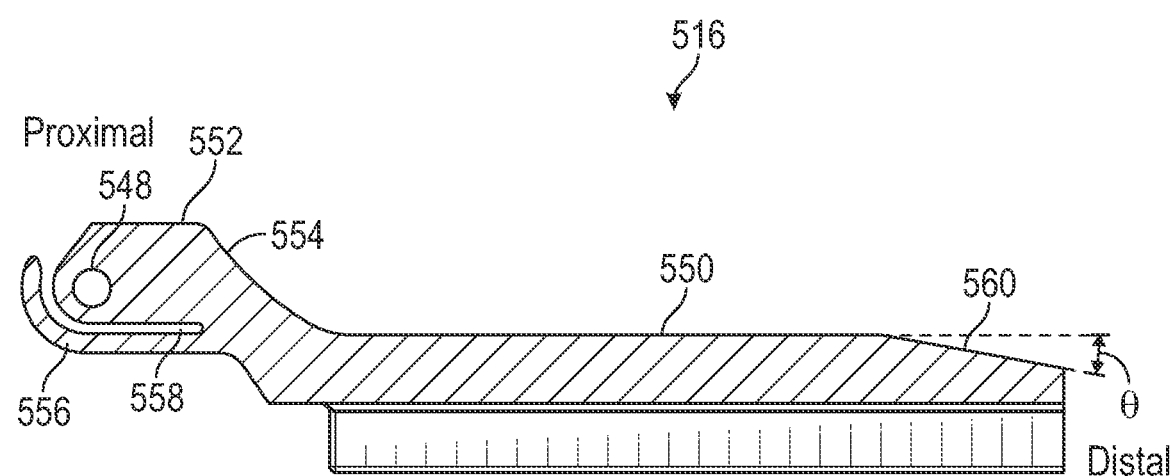
FIG. 5 illustrates an isometric view of a portion of a tower assembly, in accordance with at least one example of this disclosure.

FIG. 5 illustrates an isometric view of the lever 516, in accordance with at least one example of this disclosure. The lever 516 can include a pin bore 548, a body 550, a head 552, a neck 554, a living hinge 556 (adjacent a gap 558), and a chamfer 560. Also shown in FIG. 5 is an angle θ and orientation indicators Proximal and Distal.

The lever 516 can be consistent with the lever 116 discussed above; however, FIG. 5 shows additional details of the lever 516. For example, FIG. 5 shows how the body 550 of the lever can connect to the head 552 via the neck 554, which can be angled to offset the head 552 from the body 550 for attachment to the cam 118.

FIG. 5 also shows the living hinge 556 (or living spring), which can be spaced from the head 552 by the gap 558. The living hinge can be cantilevered from the head 552, such that the living hinge 556 can deflect with respect to the head 552. In some examples, the living hinge 556 can be under compression in the locked and the unlocked position to help prevent the lever 116 from moving without interaction by a user. Though the living hinge 556 is discussed as being a living hinge coupled to the head 552, the living hinge 556 can be other types of biasing elements, such as a spring or bar.

Figure 6:
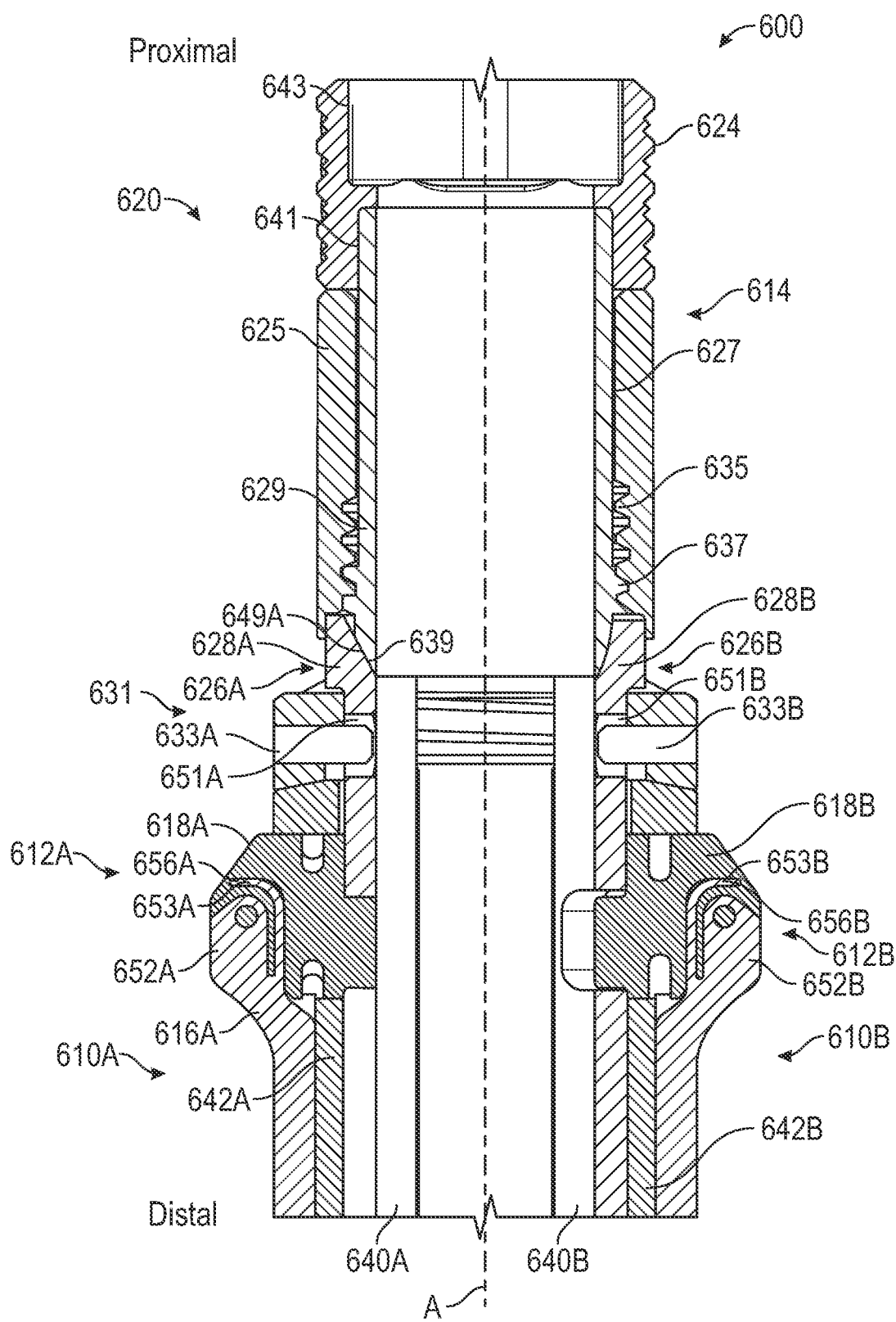
FIG. 6 illustrates a side view of a cross-section of a portion of a tower assembly, in accordance with at least one example of this disclosure.

FIG. 6 illustrates a side view of a cross-section of a portion of a tower assembly 600, in accordance with at least one example of this disclosure. The tower assembly 600 can include a cap having a piston and a pair of pins each configured to engage a sleeve of an extender to secure the cap to the extenders and can provide a tool-less interface for quickly securing the cap to the extensions for transfer of forces between the extensions and the cap. Such a cap can be included in any of the embodiments discussed above.

The tower assembly 600 can be similar to the tower assembly 100 discussed above with respect to FIGS. 1-5; similar components can therefore include similar reference numerals and names. The tower assembly 600 can include a first arm 610A, a second arm 610B, a first lock 612A, a second lock 612B, and a cap 614. The first arm 610A can include an inner sleeve 640A and an outer sleeve 642A. The second arm 610B can include an inner sleeve 640B and an outer sleeve 642B. The first lock 612A can include a lever 616A and a cam 618A. The second lock 612B can include a lever 616B and a cam 618B. The first inner sleeve 640A can include a proximal projection 628A, a chamfer 649A, and a pin bore 651A. The second inner sleeve 640B can include, a chamfer 649B, a proximal projection 628B and a pin bore 651B. The first lever 616A can include a head 652A and living hinge 656 and the first cam 618A can include a hinge slot 653A. The second lever 616B can include a head 652B and living hinge 656 and the first cam 618B can include a hinge slot 653B. The cap 614 can include a knob 624, a body 625 (including a bore 627), eyes 626A and 626B, a piston 629, a collar 631, and pins 633 (shown as pin 633A and pin 633B). The bore 627 can include a threaded portion 635. The piston 629 can include a threaded portion 637, a distal chamfer 639, and a proximal portion 641. The knob 624 can include a tool interface 643. Also shown in FIG. 6 are axis A and orientation indicators Proximal and Distal.

The proximal projection 628A and the proximal projection 628B of the inner sleeves 640A and 640B, respectively, can each be radially extending proximal projections extend from a radially outer portion of the inner sleeves 640A and 640B, respectively. The proximal projection 628A and the proximal projection 628B can be configured to insert into the eyes 626A and 626B, respectively of the cap 614.

The chamfer 649A and the chamfer 649B of the inner sleeves 640A and 640B, respectively, can be chamfers extending radially inward from a proximal portion of the inner sleeves 640A and 640B and can each be complimentary to the distal chamfer 639 of the piston 629. The pin bore 651A and the pin bore 651B of each of the inner sleeves 640A and 640B, respectively, can be bores extending through each of the inner sleeves 640A and 640B, respectively, and can each configured to receive one of the pins 633 therethrough to limit axial movement of the inner sleeves 640 with respect to the cap 614 and the outer sleeves 642.

The knob 624 can be an actuator coupled to the proximal portion of the cap body 625 and can be rotatable relative to the body 625. The knob 624 can be knurled in some examples, and can have other surface finishes to improve grip (such as milling textures). A bore of the knob 624 can be configured to receive and retain the proximal portion 641 of the piston 629 therein such that the knob 624 can be rotatable with the piston 629. The tool interface 643 can be a recess or bore extending into a proximal portion of the knob 624 and can be sized and shaped to receive a tool therein for application of torque to the knob 624. The tool interface can be hex, cross-recess, square, hexalobular, or the like. The distal chamfer 639 of the piston 629 can be a chamfer extending radially inward from a radially outer surface of a distal portion of the piston 629 and can be configured to engage the chamfers 649 of the inner sleeves 640.

The body 625 can include the bore 627 which can extend through the body 625 long the axis A. The threaded portion 635 of the body can be at a distal portion of the bore 627 and can be configured to threadably engage the threaded portion 637 of the piston such that rotation of the knob 624 and therefore the piston 641 can cause the piston to thread into and out of the bore 627 of the body 625, causing translation of the piston 627 with respect to the body 625. The knob 624 can also translate with respect to the body 625.

The collar 631 can extend distally from a distal portion of the body 625 and can extend radially outward from the body 625 to have a larger diameter than the body 625. The collar 631 can include a bore to receive the inner sleeve 640 therein. The collar 631 can, at least in part, form the eyes 626A and 626B, which can be bores or openings extending through the collar 631 and/or the body 625. The eyes 626 can be sized and shaped to receive the proximal projections 628 therein. The pins 633 can be rigid or semi-rigid members connected to the collar 631 and extending radially inward therefrom.

In operation, when the extensions 610 are in a locked position, as shown in FIG. 6, the proximal portions of the inner sleeves 640 can be inserted into the collar 631 distally-to-proximally until the proximal projections 628 engage the body 625 and/or until the proximal projections 628 engage the piston 629 and/or until the outer sleeves 642 engage a distal portion of the collar 631. The engagement(s) can align the proximal projections 628 with the eyes 626 and can align the pins 633 with the pin bores 651.

Following insertion of the inner sleeves 640 into the collar 631, the knob 624 can be rotated to translate the knob 624 and the piston 629 distally via the threaded engagement between the piston 629 and the body 625. The piston 629 can translate distally such that the chamfer 639 of the piston 629 engages the chamfers 649 of the inner sleeves 640, where the engagement can force the proximal projection 628A and 628B radially outward into the eyes 626A and 626B, respectively, to secure the cap 614 to the extenders 610. The engagement of the chamfer 639 of the piston 629 and the chamfers 649 of the inner sleeves 640 can also cause the pins 633 to each extend into the pin bores 651 to help limit axial translation of the inner sleeves 640 with respect to the cap 614. The piston 629 can be limited in distal translation via contact of the proximal portions 628 with the collar 630 and/or via contact of the pin bores 651 with the pins 633 and/or via contact between the knob 624 and the body 625. Contact between these components can also prevent distal-to-proximal translation of the cap with respect to the extensions 610 when the piston 629 is translated distally, as shown in FIG. 6, helping to prevent separation of the cap 614 from the extensions and helping to transfer forces between the cap 614 and the extensions 610.

When it is desired to remove the cap 614, the knob 624 can be rotated in a direction opposite the locking direction to translate the knob 624 and the piston 629 proximally, allowing the proximal projections 626 to move radially inward from the eyes 628 and allowing the pins 633 to disengage from the pin bores 651 so that the cap 624 can be removed from the extensions 610. Such a process can be repeated as desired.

FIG. 6 also shows how the living hinge 656 can engage with the hinge slot 653A of the first cam 618A. The hinge slot 653A can be shaped to receive and retain the living hinge 656 and to help the living hinge 656 bias the lever 616A away from the outer sleeve 642A.

NOTES AND EXAMPLES

The following, non-limiting examples, detail certain aspects of the present subject matter to solve the challenges and provide the benefits discussed herein, among others.

Example 1 is an anchor extender couplable to a bone anchor, the anchor extender comprising: an outer sleeve extending along a longitudinal axis from a proximal portion to a distal portion, the distal portion engageable with a head of a bone anchor; an inner sleeve extending along a longitudinal axis from a proximal portion to a distal portion, the inner sleeve nestable within the outer sleeve; and a lock engageable with the outer sleeve and the inner sleeve, the lock including a cam disposable in the outer sleeve and rotatable therein, the cam rotatable to translate the inner sleeve relative to the outer sleeve between a locked position and an unlocked position to secure the inner sleeve and the outer sleeve to the head of the bone anchor in the locked position and to release the inner sleeve and the outer sleeve from the head of the bone anchor in the unlocked position, the lock comprising: a lever couplable to the cam, wherein the lever is operable to rotate the cam, and wherein the lever is rotatable relative to the cam to secure the cam in the locked position, the lever including a living spring engageable with the cam to bias the lever away from the outer sleeve.

In Example 2, the subject matter of Example 1 optionally includes wherein the proximal portion of the outer sleeve includes an outer bore extending therethrough substantially orthogonally to the longitudinal axis, the outer bore configured to receive the cam therein.

In Example 3, the subject matter of Example 2 optionally includes wherein the cam includes a boss extending substantially orthogonally to the longitudinal axis, wherein the inner sleeve includes an inner bore alignable with the outer bore, the inner bore configured to receive the boss therein.

In Example 4, the subject matter of Example 3 optionally includes wherein the outer sleeve includes a collar at least partially surrounding the outer bore, wherein the cam includes a circumferential groove, and wherein the collar is configured to receive a pin therethrough to extender the circumferential groove to guide rotation of the cam relative to the outer sleeve.

In Example 5, the subject matter of any one or more of Examples 1-4 optionally include wherein the distal portion of the outer sleeve includes a distal hook extending radially inward and engageable with a notch in an outer surface of the head of the bone anchor.

In Example 6, the subject matter of Example 5 optionally includes wherein the distal portion of the inner sleeve includes a distal projection extending axially distally and insertable into a bore in a proximal portion of the head of the anchor when the inner sleeve is in the locked position.

In Example 7, the subject matter of Example 6 optionally includes wherein engagement of the distal hook with the notch of the head in the unlocked position aligns the distal projection with the bore of the proximal portion of the head.

In Example 8, the subject matter of any one or more of Examples 1-7 optionally include wherein the inner sleeve includes chamfered radially inner edges extending along the longitudinal axis and wherein the outer sleeve includes a pair of opposing rails configured to receive the chamfered edges therein to create a sliding engagement between the inner sleeve and the outer sleeve.

In Example 9, the subject matter of any one or more of Examples 1-8 optionally include wherein the outer sleeve has a radius of curvature configured to mate with an outer surface of the head of the bone anchor.

In Example 10, the subject matter of any one or more of Examples 1-9 optionally include wherein the cam includes a hinge channel configured to receive the living hinge of the lever therein.

Example 11 is an anchor tower couplable to a bone anchor, the anchor tower comprising: first and second extenders, each extender couplable to opposing sides of a bone anchor and each extender comprising: an outer sleeve extending along a longitudinal axis from a proximal portion to a distal portion, the distal portion engageable with a head of a bone anchor; an inner sleeve extending along the longitudinal axis from a proximal portion to a distal portion, the inner sleeve nestable within the outer sleeve; and a cam engageable with the outer sleeve and the inner sleeve, the cam operable to secure the inner sleeve and the outer sleeve to the head of the bone anchor; and a cap comprising: a body including a proximal portion and an opposite distal portion securable to the proximal portions of the inner sleeves of the first and second extenders; a knob coupled to the proximal portion of the body, the knob rotatable with respect to the body; and a piston located at least partially within the body and coupled to the knob, the piston translatable relative to the body in response to rotation of the knob, the piston engageable with the inner sleeves to secure the inner sleeves to the cap.

In Example 12, the subject matter of Example 11 optionally includes wherein the proximal portion of the inner sleeve of each of the first and second extenders includes a proximal projection extending radially outward therefrom.

In Example 13, the subject matter of Example 12 optionally includes wherein the distal portion of the cap includes a pair of eyes configured to engage respective proximal projections of each inner sleeve therein.

In Example 14, the subject matter of Example 13 optionally includes wherein the body of the cap includes an internal threaded portion and wherein the piston includes an external threaded portion threadably engageable with the internal threaded portion of the body, the knob rotatable to rotate the piston to translate the piston distally to engage each inner sleeve to force the proximal projection of each of the first and second extenders radially outward into the pair of eyes to secure the cap to the extenders.

In Example 15, the subject matter of Example 14 optionally includes wherein the body further comprises a pair of pins.

In Example 16, the subject matter of Example 15 optionally includes wherein the proximal portion of each inner sleeve includes a pin bore extending radially through the proximal portion, each pin bore configured to receive one of the pins therein when the piston forces the inner sleeves outward.

In Example 17, the subject matter of any one or more of Examples 11-16 optionally include wherein a distal portion of the piston includes a piston chamfer and wherein the proximal portion of the inner sleeve includes a sleeve chamfer extending radially inward from a proximal lend of the proximal portion, the sleeve chamfer configured to engage the piston chamfer when the piston is translated to engage the inner sleeves.

Example 18 is an anchor tower couplable to a bone anchor, the anchor tower comprising: a first extender couplable to a bone anchor, the extender comprising: a first outer sleeve extending along a longitudinal axis, the distal portion engageable with a head of a bone anchor; a first inner sleeve extending along the longitudinal axis, the first inner sleeve nestable within the first outer sleeve; and a first cam engageable with the first outer sleeve and the first inner sleeve, the first cam operable to secure the first inner sleeve and the first outer sleeve to the head of the bone anchor; and a second extender couplable to a bone anchor, the extender comprising: a second outer sleeve extending along the longitudinal axis, the distal portion engageable with the head of the bone anchor opposite the first outer sleeve; a second inner sleeve extending along the longitudinal axis, the second inner sleeve nestable within the second outer sleeve; and a second cam engageable with the second outer sleeve and the second inner sleeve, the second cam operable to secure the second inner sleeve and the second outer sleeve to the head of the bone anchor; and a cap comprising: a body including a proximal portion and an opposite distal portion securable to the first inner sleeve and the second inner sleeve of the first and second extenders, respectively; a knob coupled to the proximal portion of the body, the knob rotatable with respect to the body; and a piston located at least partially within the body and coupled to the knob, the piston translatable relative to the body in response to rotation of the knob, the piston engageable with the first inner sleeve and the second inner sleeve to force the first inner sleeve and the second inner sleeve outward to engage the body to secure the inner sleeves to the cap.

In Example 19, the subject matter of Example 18 optionally includes wherein the proximal portion of the inner sleeve of each of the first and second extenders includes a proximal projection extending radially outward therefrom.

In Example 20, the subject matter of Example 19 optionally includes wherein the distal portion of the cap includes a pair of eyes configured to engage respective proximal projections of each inner sleeve therein.

In Example 21, the apparatuses or method of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled,

The invention claimed is:

1. An anchor extender couplable to a bone anchor, the anchor extender comprising:
   an outer sleeve extending along a longitudinal axis from a proximal portion to a distal portion, the distal portion engageable with a head of a bone anchor;
   an inner sleeve extending along a longitudinal axis from a proximal portion to a distal portion, the inner sleeve nestable within the outer sleeve; and
   a lock engageable with the outer sleeve and the inner sleeve, the lock including a cam disposable in the outer sleeve and rotatable therein, the cam rotatable to translate the inner sleeve relative to the outer sleeve between a locked position and an unlocked position to secure the inner sleeve and the outer sleeve to the head of the bone anchor in the locked position and to release the inner sleeve and the outer sleeve from the head of the bone anchor in the unlocked position, the lock comprising:
   a lever couplable to the cam, wherein the lever is operable to rotate the cam, and wherein the lever is rotatable relative to the cam to secure the cam in the locked position, the lever including a living spring engageable with the cam to bias the lever away from the outer sleeve.

2. The anchor extender of claim 1, wherein the proximal portion of the outer sleeve includes an outer bore extending therethrough substantially orthogonally to the longitudinal axis, the outer bore configured to receive the cam therein.

3. The anchor extender of claim 2, wherein the cam includes a boss extending substantially orthogonally to the longitudinal axis, wherein the inner sleeve includes an inner bore alignable with the outer bore, the inner bore configured to receive the boss therein.

4. The anchor extender of claim 1, wherein the distal portion of the outer sleeve includes a distal hook extending radially inward and engageable with a notch in an outer surface of the head of the bone anchor.

5. The anchor extender of claim 4, wherein the distal portion of the inner sleeve includes a distal projection extending axially distally and insertable into a bore in a proximal portion of the head of the bone anchor when the inner sleeve is in the locked position.

6. The anchor extender of claim 5, wherein engagement of the distal hook with the notch of the head in the unlocked position aligns the distal projection with the bore of the proximal portion of the head.

7. The anchor extender of claim 1, wherein the inner sleeve includes chamfered radially edges extending along the longitudinal axis and wherein the outer sleeve includes a pair of opposing rails configured to receive the chamfered radially edges therein to create a sliding engagement between the inner sleeve and the outer sleeve.

8. The anchor extender of claim 1, wherein the outer sleeve has a radius of curvature configured to mate with an outer surface of the head of the bone anchor.

9. The anchor extender of claim 1, wherein the cam includes a hinge channel configured to receive the living spring of the lever therein.

10. An anchor tower couplable to a bone anchor, the anchor tower comprising:
    first and second extenders, each extender coupleable to opposing sides of a bone anchor and each extender comprising:
      an outer sleeve extending along a longitudinal axis from a proximal portion to a distal portion, the distal portion engageable with a head of a bone anchor;
      an inner sleeve extending along the longitudinal axis from a proximal portion to a distal portion, the inner sleeve nestable within the outer sleeve, the proximal portion including a proximal projection extending radially outward therefrom; and
      a cam engageable with the outer sleeve and the inner sleeve, the cam operable to secure the inner sleeve and the outer sleeve to the head of the bone anchor; and
    a cap comprising:
      a body including a pair of pins, a proximal portion, and an opposite distal portion securable to the proximal portions of the inner sleeves of the first and second extenders, the distal portion including a pair of eyes configured to engage respective proximal projections of each inner sleeve therein;
      a knob coupled to the proximal portion of the body, the knob rotatable with respect to the body; and
      a piston located at least partially within the body and coupled to the knob, the piston translatable relative to the body in response to rotation of the knob, the piston engageable with the inner sleeves to secure the inner sleeves to the cap;
    wherein the body of the cap includes an internal threaded portion and wherein the piston includes an external threaded portion threadably engageable with the internal threaded portion of the body, the knob rotatable to rotate the piston to translate the piston distally to engage each inner sleeve to force the proximal projection of each of the first and second extenders radially outward into the pair of eyes to secure the cap to the extenders; and
    wherein the proximal portion of each inner sleeve includes a pin bore extending radially through the proximal portion, each pin bore configured to receive one of the pair of pins therein when the piston forces the inner sleeves outward.

11. The anchor tower of claim 10, wherein a distal portion of the piston includes a piston chamfer and wherein the proximal portion of the inner sleeve includes a sleeve chamfer extending radially inward from a proximal end of the proximal portion, the sleeve chamfer configured to engage the piston chamfer when the piston is translated to engage the inner sleeves of the first and second extenders.

12. An anchor extender couplable to a bone anchor, the anchor extender comprising:
- an outer sleeve extending along a longitudinal axis from a proximal portion to a distal portion, the distal portion engageable with a head of a bone anchor;
- an inner sleeve extending along a longitudinal axis from a proximal portion to a distal portion, the inner sleeve nestable within the outer sleeve; and
- a lock engageable with the outer sleeve and the inner sleeve, the lock including a cam disposable in the outer sleeve and rotatable therein, the cam rotatable to translate the inner sleeve relative to the outer sleeve between a locked position and an unlocked position to secure the inner sleeve and the outer sleeve to the head of the bone anchor in the locked position and to release the inner sleeve and the outer sleeve from the head of the bone anchor in the unlocked position, the lock comprising:
  - a lever couplable to the cam, wherein the lever is operable to rotate the cam, and wherein the lever is rotatable relative to the cam to secure the cam in the locked position, the lever including a living spring engageable with the cam to bias the lever away from the outer sleeve, the cam including a boss extending substantially orthogonally to the longitudinal axis, and the cam including a circumferential groove;
  - wherein the proximal portion of the outer sleeve includes an outer bore extending therethrough substantially orthogonally to the longitudinal axis, the outer bore configured to receive the cam therein;
  - wherein the inner sleeve includes an inner bore alignable with the outer bore, the inner bore configured to receive the boss therein; and
  - wherein the outer sleeve includes a collar at least partially surrounding the outer bore, the collar configured to receive a pin therethrough to extender the circumferential groove to guide rotation of the cam relative to the outer sleeve.

13. The anchor extender of claim 12, wherein the distal portion of the outer sleeve includes a distal hook extending radially inward and engageable with a notch in an outer surface of the head of the bone anchor.

14. The anchor extender of claim 13, wherein the distal portion of the inner sleeve includes a distal projection extending axially distally and insertable into a bore in a proximal portion of the head of the bone anchor when the inner sleeve is in the locked position.

15. The anchor extender of claim 14, wherein engagement of the distal hook with the notch of the head in the unlocked position aligns the distal projection with the bore of the proximal portion of the head.

16. The anchor extender of claim 12, wherein the inner sleeve includes chamfered radially edges extending along the longitudinal axis and wherein the outer sleeve includes a pair of opposing rails configured to receive the chamfered radially edges therein to create a sliding engagement between the inner sleeve and the outer sleeve.

17. The anchor extender of claim 12, wherein the outer sleeve has a radius of curvature configured to mate with an outer surface of the head of the bone anchor.

18. The anchor extender of claim 12, wherein the cam includes a hinge channel configured to receive the living spring of the lever therein.

\* \* \* \* \*